(12) United States Patent
Dashevsky (10) Patent No.: US 9,223,046 B2
(45) Date of Patent: Dec. 29, 2015

(54) APPARATUS AND METHOD FOR CAPACITIVE MEASURING OF SENSOR STANDOFF IN BOREHOLES FILLED WITH OIL BASED DRILLING FLUID

(75) Inventor: Yuliy Aleksandrovich Dashevsky, Novosibirsk (RU)

(73) Assignee: BAKER HUGHES INCORPORATED, Houston, TX (US)

( * ) Notice: Subject to any disclaimer, the term of this patent is extended or adjusted under 35 U.S.C. 154(b) by 27 days.

(21) Appl. No.: 13/124,037

(22) PCT Filed: Oct. 1, 2010

(86) PCT No.: PCT/RU2010/000549
§ 371 (c)(1),
(2), (4) Date: Apr. 26, 2011

(87) PCT Pub. No.: WO2012/044192
PCT Pub. Date: Apr. 5, 2012

(65) Prior Publication Data
US 2012/0092015 A1    Apr. 19, 2012

(51) Int. Cl.
*G01V 3/18* (2006.01)
*G01V 3/24* (2006.01)
G01N 33/28 (2006.01)
G01N 27/02 (2006.01)
G01N 27/06 (2006.01)

(52) U.S. Cl.
CPC ............ *G01V 3/24* (2013.01); *G01N 27/026* (2013.01); *G01N 27/06* (2013.01); *G01N 33/2823* (2013.01)

(58) Field of Classification Search
CPC . G01N 33/2823; G01N 27/026; G01N 27/06; G01V 3/18; G01V 3/20; E21B 49/08

USPC ......................................................... 324/324
See application file for complete search history.

(56) References Cited

U.S. PATENT DOCUMENTS

| | | | |
|---|---|---|---|
| 2,749,503 A * | 6/1956 | Henri-Georges | 324/355 |
| 3,973,181 A * | 8/1976 | Calvert | 324/355 |
| 5,191,290 A | 3/1993 | Gianzero et al. | |
| 5,811,973 A * | 9/1998 | Meyer, Jr. | 324/338 |
| 6,057,784 A | 5/2000 | Schaaf et al. | |

(Continued)

OTHER PUBLICATIONS

Definitions of electrode, electricity, and antenna from Google definitions and Dictionary .com.*

(Continued)

*Primary Examiner* — Jermele M Hollington
*Assistant Examiner* — Christopher McAndrew
(74) *Attorney, Agent, or Firm* — Mossman Kumar & Tyler PC (57) ABSTRACT

An apparatus and method for estimating the at least one resistivity parameter using at least one processor to estimate capacitance information, wherein the capacitance information is estimated using only one selected frequency electromagnetic signal. The apparatus may include at least one measure electrode. The apparatus may also include a transverse antenna. The method may include imparting an electric current at only one selected frequency into a formation using the at least one measure electrode. The method may also include using capacitance information to estimate a standoff between the at least one measure electrode and a borehole wall. In some embodiments, the estimated capacitance information may be used to reduce errors due to eccentricity.

14 Claims, 6 Drawing Sheets

(56) References Cited

U.S. PATENT DOCUMENTS

| | | | |
|---|---|---|---|
| 6,600,321 B2* | 7/2003 | Evans | 324/369 |
| 6,819,111 B2 | 11/2004 | Fanini et al. | |
| 6,850,068 B2 | 2/2005 | Chemali et al. | |
| 7,095,232 B2* | 8/2006 | Haber et al. | 324/368 |
| 7,242,194 B2 | 7/2007 | Hayman et al. | |
| 7,250,768 B2* | 7/2007 | Ritter et al. | 324/369 |
| 7,365,545 B2 | 4/2008 | Itskovich et al. | |
| 7,397,250 B2 | 7/2008 | Bespalov et al. | |
| 7,554,329 B2 | 6/2009 | Gorek et al. | |
| 7,576,543 B2* | 8/2009 | Ritter et al. | 324/369 |
| 7,616,001 B2 | 11/2009 | Itskovich | |
| 7,652,478 B2* | 1/2010 | Pelegri | 324/338 |
| 7,689,363 B2* | 3/2010 | Itskovich et al. | 702/7 |
| 2002/0166699 A1* | 11/2002 | Evans | 175/26 |
| 2004/0104726 A1* | 6/2004 | Chemali et al. | 324/369 |
| 2005/0030035 A1* | 2/2005 | Beste et al. | 324/338 |
| 2006/0103389 A1* | 5/2006 | Bespalov et al. | 324/338 |
| 2006/0214664 A1* | 9/2006 | Folberth et al. | 324/339 |
| 2007/0046290 A1* | 3/2007 | Bespalov et al. | 324/367 |
| 2007/0279063 A1* | 12/2007 | Beard | 324/355 |
| 2008/0183392 A1 | 7/2008 | Forgang | |
| 2008/0272789 A1* | 11/2008 | San Martin et al. | 324/355 |
| 2008/0288171 A1* | 11/2008 | Itskovich et al. | 702/7 |
| 2009/0302854 A1* | 12/2009 | Forgang et al. | 324/355 |

OTHER PUBLICATIONS

Heisig, G., et al., "Downhole Diagnosis of Drilling Dynamics Data Provides New Level Drilling Process Control to Driller," SPE 49206, pp. 649-648, 1998 SPE Annual Technology Conference and Exhibition, New Orleans, LA (Sep. 1998).

* cited by examiner

APPARATUS AND METHOD FOR CAPACITIVE MEASURING OF SENSOR STANDOFF IN BOREHOLES FILLED WITH OIL BASED DRILLING FLUID

FIELD OF THE DISCLOSURE

This disclosure generally relates to exploration for hydrocarbons involving electrical investigations of a borehole penetrating an earth formation. More specifically, this disclosure relates to estimating a standoff between a measure electrode and a borehole wall using only one selected frequency electromagnetic signal.

BACKGROUND OF THE DISCLOSURE

Electrical earth borehole logging is well known and various devices and various techniques have been described for this purpose. Electromagnetic induction and wave propagation logging tools are commonly used for determination of electrical properties of formations surrounding a borehole. These logging tools give measurements of apparent resistivity (or conductivity) of the formation that, when properly interpreted, are diagnostic of the petrophysical properties of the formation and the fluids therein. Broadly speaking, there are two categories of devices used in electrical logging devices. In the first category, a transmitter (such as a current electrode) is uses in conjunction with a diffuse return electrode (such as the tool body). A measured electric current flows in a circuit that connects a current source to the transmitter, through the earth formation to the return electrode and back to the current source in the tool. In inductive measuring tools, an antenna within the measuring instrument induces a current flow within the earth formation. The magnitude of the induced current is detected using either the same antenna or a separate receiver antenna. The present disclosure belongs to the first category.

With tools in the first category, it is desirable to know standoff distance between a measure electrode and a wall of a borehole. While high frequency electromagnetic signals are used to estimate the complex impedance between a measure electrode and a return electrode on a downhole tool, the resistivity of the formation may make obtaining accurate standoff estimates difficult. Additionally, electromagnetic induction resistivity well logging data may be limited by the accuracy of standoff information. The present disclosure addresses these difficulties.

SUMMARY OF THE DISCLOSURE

In aspects, the present disclosure is related to methods and apparatuses for estimating a resistivity parameter using estimated capacitance information generated using only one selected frequency electromagnetic signal.

One embodiment according to the present disclosure may include a method of estimating at least one resistivity parameter of a formation, comprising: conveying a bottom hole assembly configured for induction measurement into a borehole; and using a processor for estimating the at least one resistivity parameter using: (i) an induction estimate made by the bottom hole assembly and (ii) a capacitance estimated using only one selected frequency electromagnetic signal.

Another embodiment according to the present disclosure may include an apparatus for estimating at least one resistivity parameter of a formation, comprising: a carrier; a bottom hole assembly disposed on the carrier, the bottom hole assembly comprising: an electromagnetic induction tool, and at least one measure electrode; and a power source in electrical communication with the at least one measure electrode and configured to provide an electromagnetic signal to the at least one measure electrode at only one selected frequency.

Examples of the more important features of the disclosure have been summarized rather broadly in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein.

DETAILED DESCRIPTION

This disclosure generally relates to exploration for hydrocarbons involving electrical investigations of a borehole penetrating an earth formation. More specifically, this disclosure relates to estimating a resistivity parameter using estimated capacitance information generated using only one selected frequency electromagnetic signal.

Capacitance information may be used to estimate a standoff distance between a measure electrode and a borehole wall, where the standoff represents the thickness of a drilling fluid layer that is situated between the borehole wall and the measure electrode. Herein, "information" may include raw data, processed data, analog signals, and digital signals. An electric current may be imparted from the measure electrode into a formation across a standoff, and a complex impedance may be estimated based on the voltage magnitude and phase and the magnitude and phase of the imparted current. At low frequencies, about 1 kHz) the formation may contribute substantially zero capacitance to the complex impedance. Thus, the estimated impedance may be used to estimate the standoff.

The measure electrode may be positioned on a bottom hole assembly (BHA) or tool body configured to be conveyed into a borehole as part of a drill string. A return electrode may be positioned in physical contact with the formation or along the surface of the BHA. The mutual capacitance between the two electrodes may be estimated in real-time. The return electrode may be placed near a drill bit at the end of the drill string or on the BHA.

An electromagnetic signal imparted into the formation from the measure electrode at a low frequency, around 1000 Hz, may be used to estimate the mutual capacitance between the electrodes. The low frequency signal may depend only on the standoff distance and the dielectric permittivity of a non-conductive drilling fluid in the borehole. At low frequencies, there may be little or no capacitance contributed by the formation. Both a capacitance log and an electromagnetic signal log may have a common sensor point in some embodiments. The unknown standoff may be estimated using a real-time inversion of the capacitance data. Formation resistivity effects may be reduced or eliminated though signal processing after the data inversion for the standoff value.

For example, if the frequency of operation is about 1000 Hz then the non-conductive drilling fluid resistivity and dielectric permittivity can be estimated as ~$10^7$ Ohm·m and 3-7 respectively. Suppose that the electrode radius R is about 0.02 m. If it is the case, then the mutual capacitance C between the borehole wall and the electrode is about 10 pF. Under these assumptions a capacitive resistance $X_c$ may be estimated as follows:

$$X_c = \frac{1}{2\pi f C} = \frac{1}{6.28 \cdot 1000 \cdot 10 \cdot 10^{-12}} = \frac{10^8}{6.28} \approx 10^7 \text{ Ohm}$$

The measured capacitance may be a function of the standoff and the permittivity of non-conductive drilling fluid only, provided that the galvanic resistance at the contact between the rock and the bit is much smaller than the capacitive resistance. In some embodiments, a standoff may be related to an estimated capacitance using a sensitivity function, such as follows:

$$\eta_H = \frac{\partial \ln C}{\partial \ln H},$$

where $\eta_H$ is the sensitivity function, C is the estimated capacitance, and H is the standoff.

Figure 1:
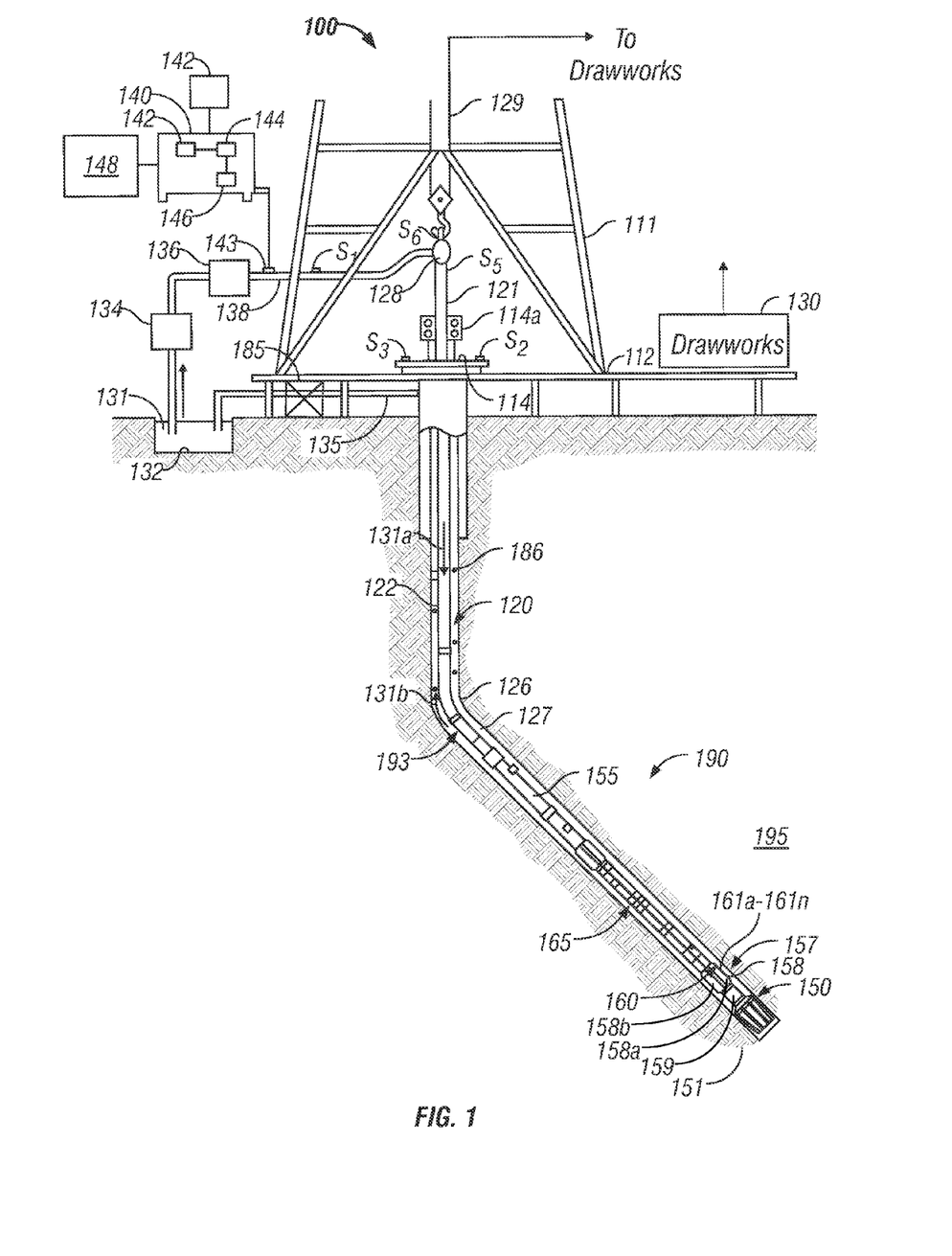
FIG. 1 shows a schematic of an imaging tool deployed in a borehole along a drill string according to one embodiment of the present disclosure.

FIG. 1 is a schematic diagram of an exemplary drilling system 100 that includes a drill string having a drilling assembly attached to its bottom end that includes a steering unit according to one embodiment of the disclosure. FIG. 1 shows a drill string 120 that includes a drilling assembly or bottom-hole assembly (BHA) 190 conveyed by a carrier 122 in a borehole 126. The drilling system 100 includes a conventional derrick 111 erected on a platform or floor 112 which supports a rotary table 114 that is rotated by a prime mover, such as an electric motor (not shown), at a desired rotational speed. The carrier 122, such as jointed drill pipe, having the drilling assembly 190, attached at its bottom end extends from the surface to the bottom 151 of the borehole 126. A drill bit 150, attached to drilling assembly 190, disintegrates the geological formations when it is rotated to drill the borehole 126. The drill string 120 is coupled to a drawworks 130 via a Kelly joint 121, swivel 128 and line 129 through a pulley. Drawworks 130 is operated to control the weight on bit ("WOB"). The drill string 120 may be rotated by a top drive (not shown) instead of by the prime mover and the rotary table 114. Alternatively, a coiled-tubing may be used as the tubing 122. A tubing injector 114a may be used to convey the coiled-tubing having the drilling assembly attached to its bottom end. The operations of the drawworks 130 and the tubing injector 114a are known in the art and are thus not described in detail herein.

A suitable drilling fluid 131 (also referred to as the "mud") from a source 132 thereof, such as a mud pit, is circulated under pressure through the drill string 120 by a mud pump 134. The drilling fluid 131 passes from the mud pump 134 into the drill string 120 via a desurger 136 and the fluid line 138. The drilling fluid 131a from the drilling tubular 122 discharges at the borehole bottom 151 through openings in the drill bit 150. The returning drilling fluid 131b circulates uphole through the annular space 127 between the drill string 120 and the borehole 126 and returns to the mud pit 132 via a return line 135 and drill cutting screen 185 that removes the drill cuttings 186 from the returning drilling fluid 131b. A sensor $S_1$ in line 138 provides information about the fluid flow rate. A surface torque sensor $S_2$ and a sensor $S_3$ associated with the drill string 120 respectively provide information about the torque and the rotational speed of the drill string 120. Tubing injection speed is determined from the sensor $S_5$, while the sensor $S_6$ provides the hook load of the drill string 120.

In some applications, the drill bit 150 is rotated by only rotating the drill pipe 122. However, in many other applications, a downhole motor 155 (mud motor) disposed in the drilling assembly 190 also rotates the drill bit 150. The rate of penetration for a given BHA 190 largely depends on the WOB or the thrust force on the drill bit 150 and its rotational speed.

The mud motor 155 is coupled to the drill bit 150 via a drive shaft disposed in a bearing assembly 157. The mud motor 155 rotates the drill bit 150 when the drilling fluid 131 passes through the mud motor 155 under pressure. The bearing assembly 157, in one aspect, supports the radial and axial forces of the drill bit 150, the down-thrust of the mud motor 155 and the reactive upward loading from the applied weight-on-bit.

A surface control unit or controller 140 receives signals from the downhole sensors and devices via a sensor 143 placed in the fluid line 138 and signals from sensors $S_1$-$S_6$ and other sensors used in the system 100 and processes such signals according to programmed instructions provided to the surface control unit 140. The surface control unit 140 displays desired drilling parameters and other information on a display/monitor 142 that is utilized by an operator to control the drilling operations. The surface control unit 140 may be a computer-based unit that may include a processor 147 (such as a microprocessor), a storage device 144, such as a solid-state memory, tape or hard disc, and one or more computer programs 146 in the storage device 144 that are accessible to the processor 147 for executing instructions contained in such programs. The surface control unit 140 may further communicate with a remote control unit 148. The surface control unit 140 may process data relating to the drilling operations, data from the sensors and devices on the surface, data received from downhole, and may control one or more operations of the downhole and surface devices. The data may be transmitted in analog or digital form.

The BHA may also contain formation evaluation sensors or devices (also referred to as measurement-while-drilling ("MWD") or logging-while-drilling ("LWD") sensors) determining resistivity, density, porosity, permeability, acoustic properties, nuclear-magnetic resonance properties, formation pressures, properties or characteristics of the fluids downhole and other desired properties of the earth formation 195 surrounding the drilling assembly 190. Such sensors are generally known in the art and for convenience are generally denoted herein by numeral 165. The drilling assembly 190 may further include a variety of other sensors and devices 159 for determining one or more properties of the BHA (such as vibration, bending moment, acceleration, oscillations, whirl, stick-slip, etc.) and drilling operating parameters, such as weight-on-bit, fluid flow rate, pressure, temperature, rate of penetration, azimuth, tool face, drill bit rotation, etc.) For convenience, all such sensors are denoted by numeral 159.

The drilling assembly 190 includes a steering apparatus or tool 158 for steering the drill bit 150 along a desired drilling path. In one aspect, the steering apparatus may include a steering unit 160, having a number of force application members 161a-161n, wherein the steering unit is at partially integrated into the drilling motor. In another embodiment the steering apparatus may include a steering unit 158 having a bent sub and a first steering device 158a to orient the bent sub in the wellbore and the second steering device 158b to maintain the bent sub along a selected drilling direction.

The MWD system may include sensors, circuitry and processing software and algorithms for providing information about desired dynamic drilling parameters relating to the BHA, drill string, the drill bit and downhole equipment such as a drilling motor, steering unit, thrusters, etc. Exemplary sensors include, but are not limited to, drill bit sensors, an RPM sensor, a weight on bit sensor, sensors for measuring mud motor parameters (e.g., mud motor stator temperature, differential pressure across a mud motor, and fluid flow rate through a mud motor), and sensors for measuring acceleration, vibration, whirl, radial displacement, stick-slip, torque, shock, vibration, strain, stress, bending moment, bit bounce, axial thrust, friction, backward rotation, BHA buckling and radial thrust. Sensors distributed along the drill string can measure physical quantities such as drill string acceleration and strain, internal pressures in the drill string bore, external pressure in the annulus, vibration, temperature, electrical and magnetic field intensities inside the drill string, bore of the drill string, etc. Suitable systems for making dynamic downhole measurements include COPILOT, a downhole measurement system, manufactured by BAKER HUGHES INCORPORATED. Suitable systems are also discussed in "Downhole Diagnosis of Drilling Dynamics Data Provides New Level Drilling Process Control to Driller", SPE 49206, by G. Heisig and J. D. Macpherson, 1998.

The MWD system 100 can include one or more downhole processors at a suitable location such as 193 on the BHA 190. The processor(s) can be a microprocessor that uses a computer program implemented on a suitable machine readable medium that enables the processor to perform the control and processing. The machine readable medium may include ROMs, EPROMs, EAROMs, EEPROMs, Flash Memories, RAMs, Hard Drives and/or Optical disks. Other equipment such as power and data buses, power supplies, and the like will be apparent to one skilled in the art. In one embodiment, the MWD system utilizes mud pulse telemetry to communicate data from a downhole location to the surface while drilling operations take place. The surface processor 147 can process the surface measured data, along with the data transmitted from the downhole processor, to evaluate formation lithology. While a drill string 120 is shown as a conveyance system for sensors 165, it should be understood that embodiments of the present disclosure may be used in connection with tools conveyed via rigid (e.g. jointed tubular or coiled tubing) as well as non-rigid (e. g. wireline, slickline, e-line, etc.) conveyance systems. A downhole assembly (not shown) may include a bottomhole assembly and/or sensors and equipment for implementation of embodiments of the present disclosure on either a drill string or a wireline.

Figure 2:
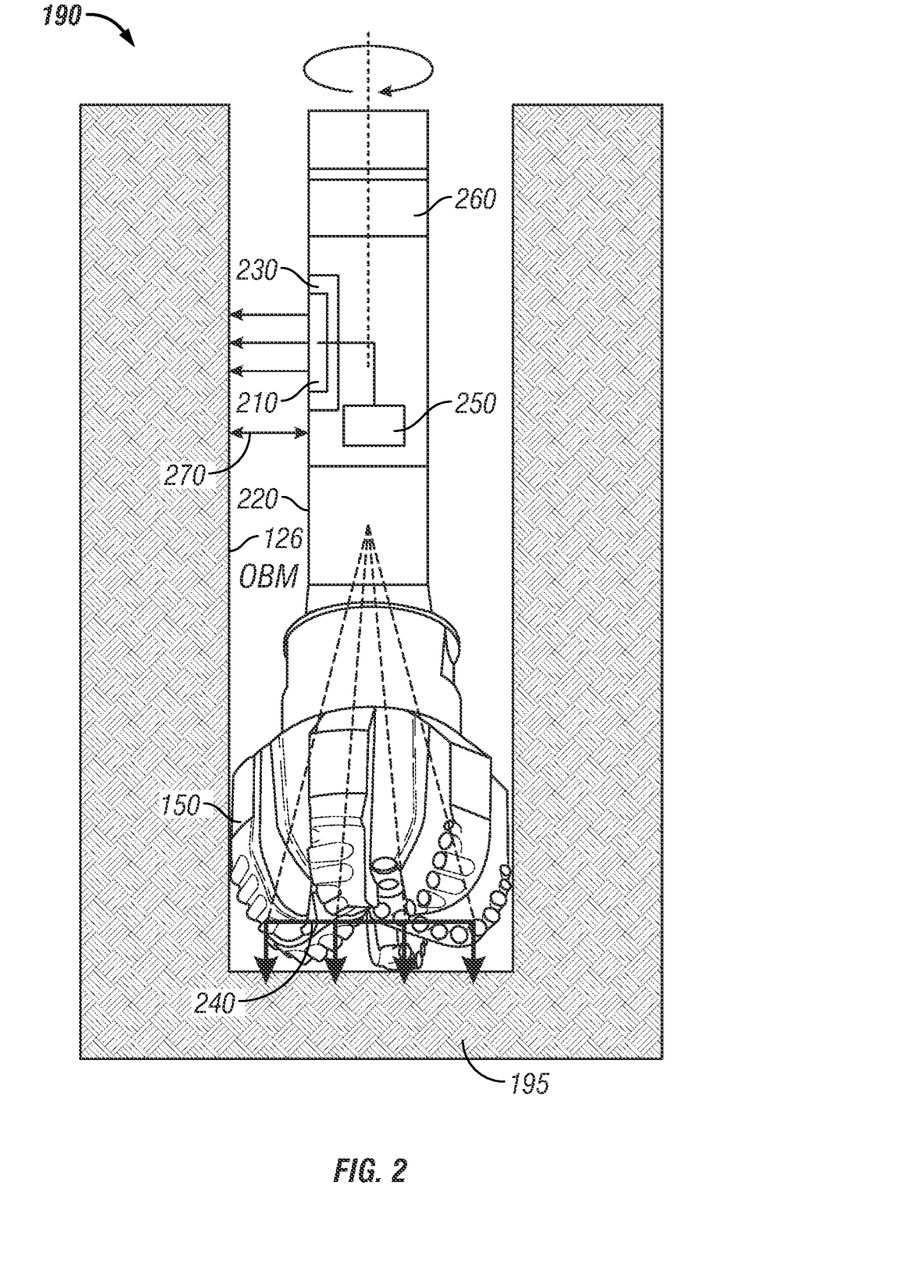
FIG. 2 shows a schematic close up of an bottom hole assembly deployed in a borehole according to one embodiment of the present disclosure.

FIG. 2 shows a schematic of an exemplary BHA 190 for one embodiment according to the present disclosure. The BHA 190 may include at least one measure electrode 210 disposed along the surface 220 of the bottom hole assembly 190. The at least one measure electrode 210 may be electrically isolated from the BHA 190 by an isolating material 230. A return electrode 240 may be disposed on drill bit 150, such that the return electrode 240 may be in contact with formation 195. A measurement device 250 may include a power source configured to impart an electric current into formation 195 through the at least one measure electrode 210. The electric current may cross a standoff 270 between the at least one measure electrode 210 and the borehole wall 126. After passing though the formation 195, the electric current may return though the return electrode 240 and drill bit 150. In some embodiments, BHA 190 may include multiple measure electrodes 210 and be configured to generate capacitance information along multiple azimuthal directions. The BHA 190 may also include an electromagnetic logging tool 260. Electromagnetic logging tool 260 may include one or more transmitter coils and one or more receiver coils. The logging tool 260 may include vertical and/or transverse coils, where vertical is parallel with the longitudinal axis of the borehole 126. BHA 190 may be used to generate information for an image or merely a log of at least one resistivity parameter. The at least one resistivity parameter may include, but is not limited to, one of: (i) conductivity, (ii) permittivity, (iii) dielectric constant, (iv) impedance, (v) capacitance, and (vi) inductance.

Figure 3:
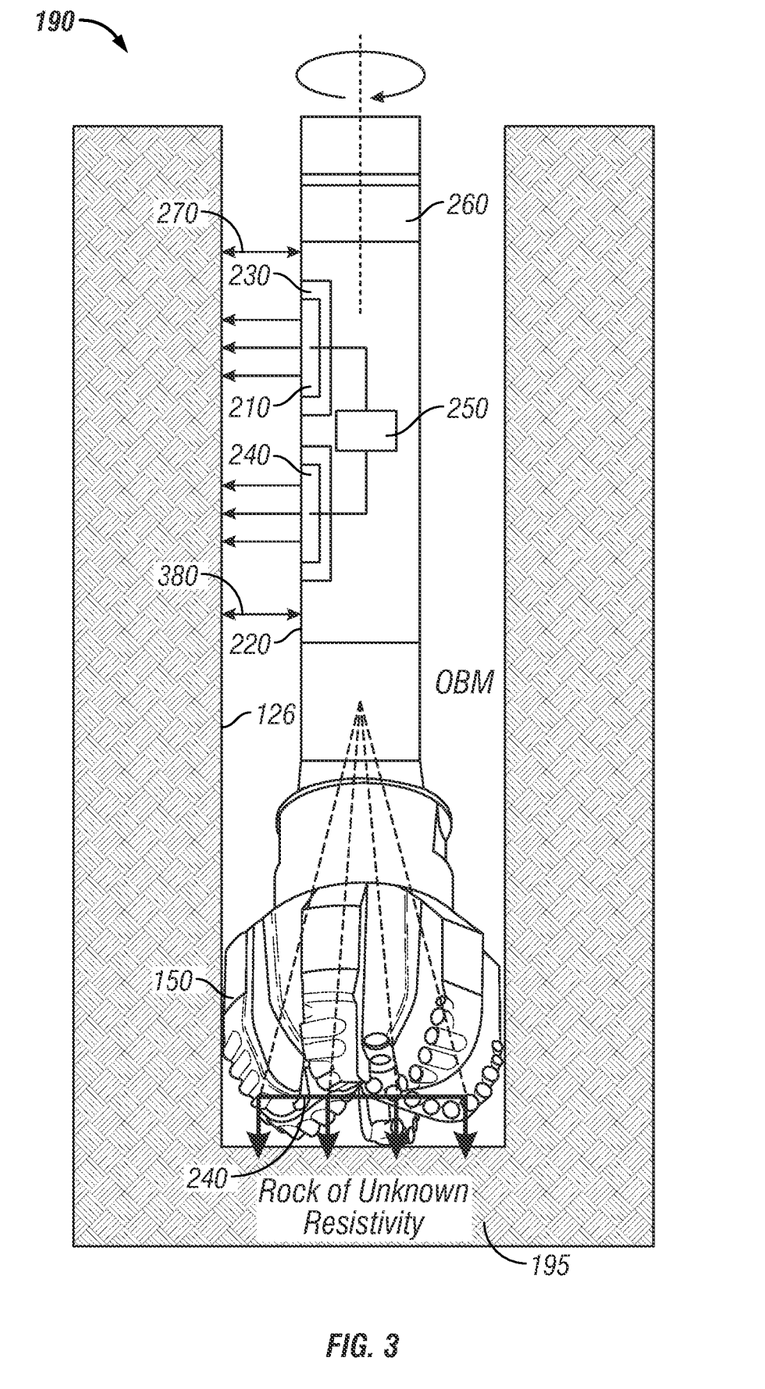
FIG. 3 shows a schematic close up of a bottom hole assembly deployed in a borehole according to another embodiment of the present disclosure.

In an alternative embodiment of the disclosure, shown in FIG. 3, BHA 190 may have one or more return electrodes 240 disposed along the surface 220. Since the one or more return electrodes 240 may have a standoff 380, the electric current imparted from the at least one measure electrode 210 may have to cross standoff 270 to enter the formation 195 and cross standoff 380 to return from the formation 195 to the one or more return electrodes 240.

Figure 4:
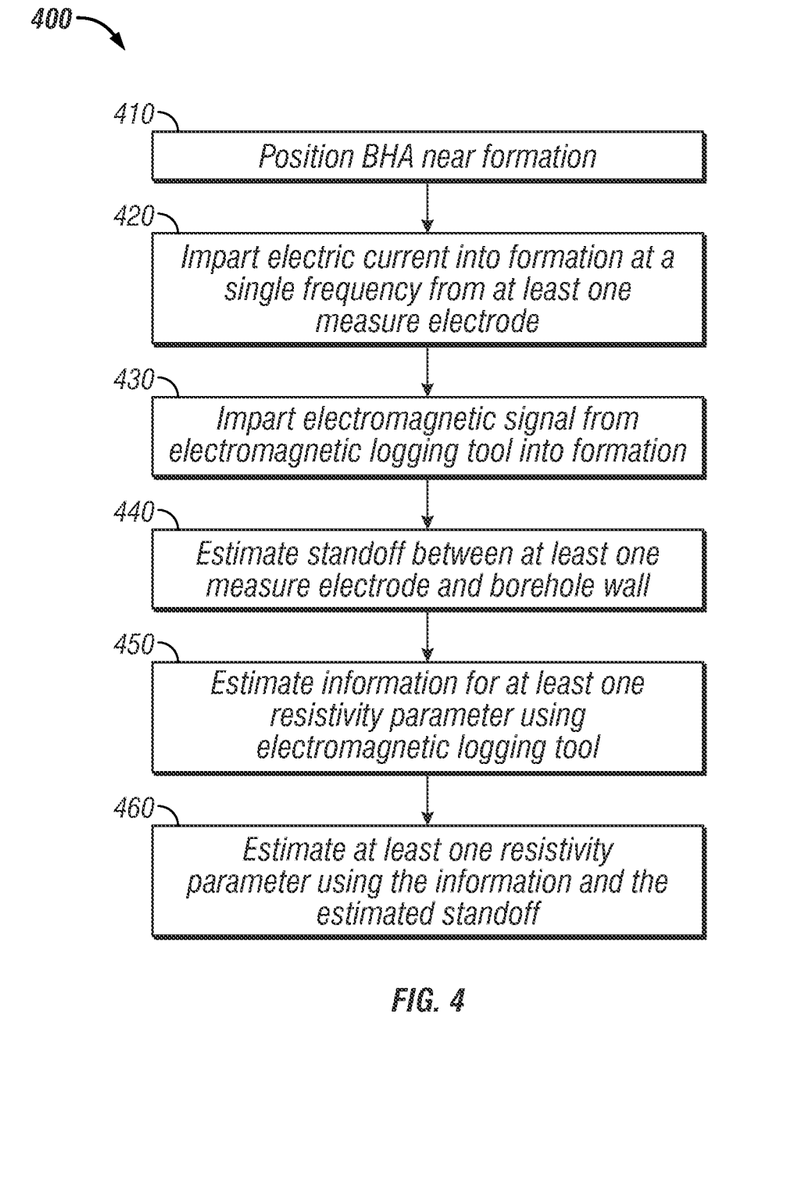
FIG. 4 shows a flow chart of a method for estimating at least one resistivity parameter of a formation according to one embodiment of the present disclosure.

FIG. 4 shows an exemplary method 400 according to one embodiment of the present disclosure. In method 400, BHA 190 may be positioned within a borehole 126 adjacent to a formation 195 in step 410. Then, in step 420, an electric current may be imparted into the formation 195 at a single frequency from at least one measure electrode 210. In step 430, an electromagnetic signal may be imparted into the formation 195 using electromagnetic logging tool 260. In step 440, a processor may estimate the standoff between the at least one measure electrode 210 and the borehole wall 126. The estimated standoff may be based on the mutual capacitance between the at least one measure electrode 210 and the return electrode 240. However, when a low frequency is used (~1000 Hz), the effect on an estimated impedance due to a capacitance of the non-standoff path (not part of standoff 270 or standoff 380) may be substantially zero. The non-standoff path may be made up of the path the signal may take through the formation. In step 450, information about at least one resistivity parameter may be estimated using a signal received by the electromagnetic logging tool 260. In some embodiments, the logging tool 260 may include transverse coils that may be affected by eccentricity. Herein, eccentricity may refer: (i) a non-circular borehole, (ii) an eccentric BHA in a circular borehole, and (iii) a circular BHA positioned off center in a circular borehole. Estimated standoffs may be used to reduce errors due to borehole eccentricity. In step 460, at least one resistivity parameter may be estimated using the information and the estimated standoff. In some embodiments, steps 430, 450, and 460 may be optional. The estimated standoff may be an estimate of at least one of: (i)

standoff 270, (ii) standoff 380, and (iii) standoff 270 and standoff 380 combined. In some embodiments, the standoff 270, 380 may be estimated to provide 360 degrees of azimuthal coverage. Correction for the effect of the estimated standoff may be done by including the standoff as part of a model used for inverting the electromagnetic information.

Figure 5:
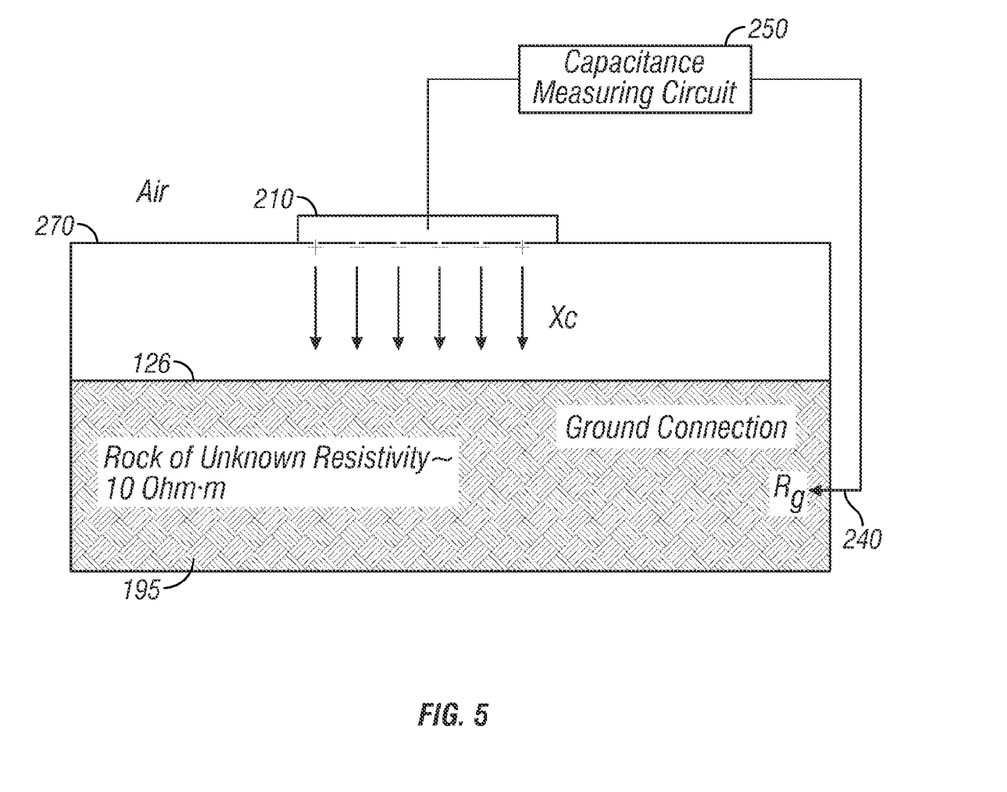
FIG. 5 shows an exemplary model for the schematic diagram of FIG. 2.

FIG. 5 shows an exemplary model for mathematically modeling the embodiment from FIG. 2 according to the present disclosure. The capacitance between the borehole wall 126 and at least one measure electrode 210 may be estimated by measurement device 250. In the model, there may be two horizontal layers, which may be 1) the boundary line of the borehole wall 126 and standoff 270 and 2) the boundary line of standoff 270 and at least one measure electrode 210, which may represents an infinitely thin electrode. It may be assumed that the standoff 270 include a non-conductive medium, such as air or non-conductive drilling fluid. The reactive component Xc of the complex impedance may be dominant across standoff 270, while the resistive component Rg of the complex impedance may be dominant in the formation 195., such that, at the selected frequency, the impedance of the circuit may be expressed as:

$$R+jX = R_{formation} + R_{standoff} + j(X_{formation} + X_{standoff}) \approx R_{formation} + jX_{standoff}$$

Figure 6A:
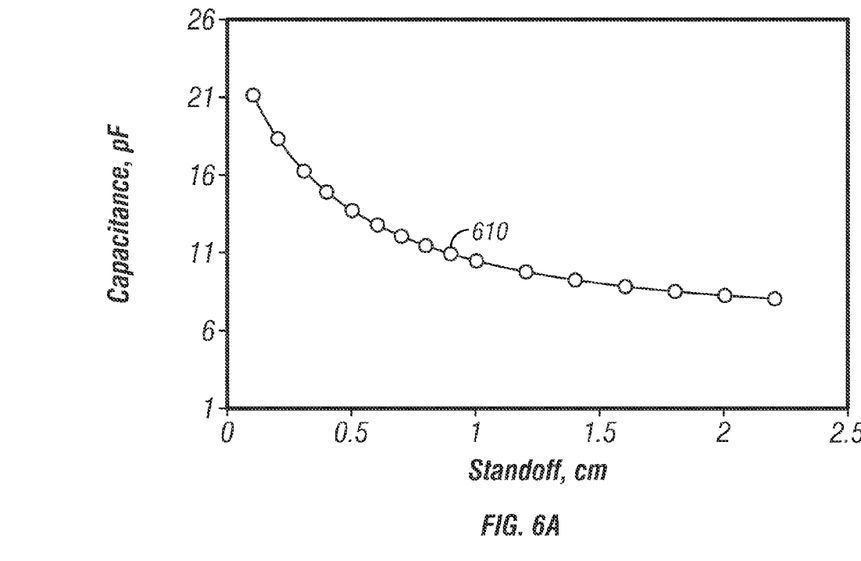
FIG. 6A graphically illustrates a relationship between estimated capacitance and standoff using the exemplary model from FIG. 4.
Figure 6B:
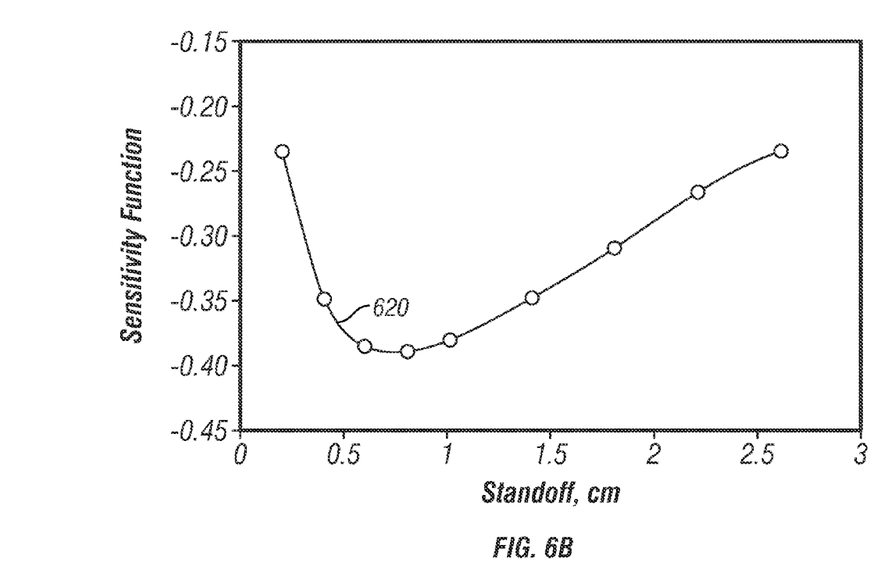
FIG. 6B graphically illustrates a curve denoting the relationship between a sensitivity function and a standoff using the exemplary model from FIG. 4.

FIG. 6A illustrates a relationship 610 between estimated capacitance and standoff 270 from the model shown in FIG. 4. FIG. 6B illustrates a curve 620 denoting the relationship between a sensitivity function and standoff 270 according the model from FIG. 4.

Implicit in the processing of the data is the use of a computer program implemented on a suitable machine readable medium that enables the processor to perform the control and processing. The term processor as used in this application is intended to include such devices as field programmable gate arrays (FPGAs). The machine readable medium may include ROMs, EPROMs, EAROMs, Flash Memories and Optical disks. As noted above, the processing may be done downhole or at the surface, by using one or more processors. In addition, results of the processing, such as an image of a resistivity parameter, can be stored on a suitable medium.

While the foregoing disclosure is directed to the one mode embodiments of the disclosure, various modifications will be apparent to those skilled in the art. It is intended that all variations be embraced by the foregoing disclosure.

The invention claimed is:

1. A method of estimating at least one resistivity parameter of a formation, comprising:
   conveying a bottom hole assembly configured for electromagnetic formation measurement into a borehole; and
   using at least one processor to:
   (i) measure a capacitance using only one selected frequency electromagnetic signal between the formation and at least one measure electrode associated with the bottom hole assembly;
   (ii) estimate a standoff between the at least one measure electrode and a borehole wall using the capacitance by using an inversion of a plurality of capacitance measurements; and
   (iii) estimate the at least one resistivity parameter using the estimated standoff and information about the at least one resistivity parameter estimated from an electromagnetic signal received by the bottom hole assembly from the formation.

2. The method of claim 1, wherein the selected frequency is selected such that the formation has a capacitance of substantially zero.

3. The method of claim 1, further comprising:
   imparting an electric current into the formation using at least one measure electrode.

4. The method of claim 1, further comprising:
   positioning the bottom hole assembly in a borehole in the formation.

5. An apparatus for estimating at least one resistivity parameter of a formation, comprising:
   a carrier;
   a bottom hole assembly disposed on the carrier, the bottom hole assembly comprising:
   an electromagnetic induction tool, and
   at least one measure electrode;
   a power source in electrical communication with the at least one measure electrode and configured to provide an electromagnetic signal to the at least one measure electrode at only one selected frequency; and
   at least one processor; and
   instructions on a non-transitory medium accessible to the at least one processor;
   wherein the at least one processor is configured to execute the instructions to:
   (i) measure a capacitance using the only one selected frequency electromagnetic signal between the formation and the at least one measure electrode;
   (ii) estimate a standoff between the at least one measure electrode and a borehole wall using the capacitance by using an inversion of a plurality of capacitance measurements; and
   (iii) estimate the at least one resistivity parameter using the estimated standoff and information about the at least one resistivity parameter estimated from an electromagnetic signal received by the electromagnetic induction tool.

6. The apparatus of claim 5, wherein the selected frequency is selected such that an effect on an estimated impedance due to a capacitance of the formation is substantially zero.

7. The apparatus of claim 5, further comprising:
   at least one return electrode disposed on one of: (i) a drill bit and (ii) the bottom hole assembly.

8. The apparatus of claim 5, wherein the bottom hole assembly further comprises:
   at least one transverse antenna.

9. The apparatus of claim 5, wherein the power source is disposed in the bottom hole assembly tool.

10. The apparatus of claim 5, wherein the power source is one of: a current source and a voltage source.

11. The method of claim 1, wherein the inversion depends only on the standoff and a permittivity of non-conductive drilling fluid between the at least one measure electrode and the borehole wall.

12. The apparatus of claim 5, wherein the inversion depends only on the standoff and a permittivity of non-conductive drilling fluid between the at least one measure electrode and the borehole wall.

13. The apparatus of claim 5, wherein the at least one processor is configured to estimate the standoff by modeling the standoff using a sensitivity function.

14. A method of estimating at least one resistivity parameter of a formation, comprising:
   conveying a bottom hole assembly configured for electromagnetic formation measurement into a borehole; and
   using at least one processor to:
   (i) measure a capacitance using only one selected frequency electromagnetic signal between the formation and at least one measure electrode associated with the bottom hole assembly;

(ii) estimate a standoff between the at least one measure electrode and a borehole wall using the capacitance by modeling the standoff using a sensitivity function; and (iii) estimate the at least one resistivity parameter using the estimated standoff and information about the at least one resistivity parameter estimated from an electromagnetic signal received by the bottom hole assembly from the formation.

* * * * *